United States Patent
Dierking et al.

(10) Patent No.: US 8,021,413 B2
(45) Date of Patent: Sep. 20, 2011

(54) LOW PROFILE MEDICAL DEVICE

(75) Inventors: William Kurt Dierking, West Lafayette, IN (US); Blayne A. Roeder, Lafayette, IN (US); Alan R. Leewood, Lafayette, IN (US); Steven J. Charlebois, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 16 days.

(21) Appl. No.: 12/337,452

(22) Filed: Dec. 17, 2008

(65) Prior Publication Data

US 2009/0177265 A1   Jul. 9, 2009

Related U.S. Application Data (60) Provisional application No. 61/016,942, filed on Dec. 27, 2007.

(51) Int. Cl.
*A61F 2/06* (2006.01)
(52) U.S. Cl. ...................... 623/1.13; 623/1.35
(58) Field of Classification Search .................. 623/1.1, 623/1.13–1.14, 1.21, 1.23, 1.25, 1.35–1.36
See application file for complete search history.

(56) References Cited

U.S. PATENT DOCUMENTS

| 5,282,484 | A | 2/1994 | Reger |
| 5,571,170 | A | 11/1996 | Palmaz et al. |
| 5,676,696 | A | 10/1997 | Marcade |
| 5,716,365 | A | 2/1998 | Goicoechea et al. |
| 5,723,004 | A | 3/1998 | Dereume et al. |
| 5,728,131 | A | 3/1998 | Frantzen et al. |
| 5,782,904 | A | 7/1998 | White et al. |
| 5,824,037 | A | 10/1998 | Fogarty et al. |
| 5,824,040 | A | 10/1998 | Cox et al. |
| 5,843,158 | A | 12/1998 | Lenker et al. |
| 6,099,558 | A | 8/2000 | White et al. |
| 6,129,756 | A | 10/2000 | Kugler et al. |
| 6,162,246 | A | 12/2000 | Barone |

(Continued)

FOREIGN PATENT DOCUMENTS

EP    0 461 791 A1    6/1991

(Continued)

OTHER PUBLICATIONS

PCT International Search Report for PCT/US2008/013850, May 8, 2009.

(Continued)

*Primary Examiner* — William H Matthews
(74) *Attorney, Agent, or Firm* — Brinks Hofer Gilson & Lione (57) ABSTRACT

The disclosure relates to an intraluminal medical device. The medical device comprises a main graft, a first extension graft, and a second extension graft. The main graft comprises a proximal end, a distal end, and a body extending between the proximal end and distal end. The distal end of the main graft comprises a first branch and a second branch, the branches extending distally from the body. The first and second extension grafts comprise at least one stent and have a body reinforcing portion and a branch reinforcing portion. The body reinforcing portions have a larger expanded dimension than the expanded dimension of the respective branch reinforcing portion. The body reinforcing portions, together, have an expanded dimension that is generally equal to the expanded dimension of the outer graft body.

21 Claims, 6 Drawing Sheets

U.S. PATENT DOCUMENTS

| | | |
|---|---|---|
| 6,293,969 B1 | 9/2001 | Chuter |
| 6,334,869 B1 | 1/2002 | Leonhardt et al. |
| 6,383,171 B1 | 5/2002 | Gifford et al. |
| 6,409,756 B1 | 6/2002 | Murphy |
| 6,451,053 B1 | 9/2002 | Dehdashtian et al. |
| 6,478,813 B1 * | 11/2002 | Keith et al. .............. 623/1.11 |
| 6,592,614 B2 | 7/2003 | Lenker et al. |
| 6,695,875 B2 | 2/2004 | Stelter et al. |
| 6,730,119 B1 | 5/2004 | Smalling |
| 6,918,926 B2 | 7/2005 | Letort |
| 6,942,691 B1 | 9/2005 | Chuter |
| 7,122,052 B2 | 10/2006 | Greenhalgh |
| 7,135,037 B1 | 11/2006 | Chuter et al. |
| 2005/0043784 A1 | 2/2005 | Yampolsky |
| 2006/0100686 A1 | 5/2006 | Bolduc et al. |
| 2007/0055345 A1 | 3/2007 | Arbefeuille |

FOREIGN PATENT DOCUMENTS

| | | |
|---|---|---|
| WO | WO 98/44873 | 10/1998 |
| WO | WO 2005/032340 | 4/2005 |

OTHER PUBLICATIONS

PCT Written Opinion for PCT/US2008/013850, May 8, 2009.

* cited by examiner

LOW PROFILE MEDICAL DEVICE

PRIORITY CLAIM

This application claims the benefit of provisional U.S. Patent Application Ser. No. 61/016,942, filed Dec. 27, 2007, which is incorporated herein by reference in its entirety.

TECHNICAL FIELD

This disclosure relates to endovascular treatments and procedures and, in particular, an intraluminal prosthesis such as a stent graft assembly having a low delivery profile.

BACKGROUND OF THE DISCLOSURE

Aneurysms occur in blood vessels in locations where, due to age, disease or genetic predisposition, insufficient blood vessel strength or resiliency may cause the blood vessel wall to weaken and/or lose its shape as blood flows it, resulting in a ballooning or stretching of the blood vessel at the limited strength/resiliency location, thus forming an aneurysmal sac. Left untreated, the blood vessel wall may continue to expand to the point where the remaining strength of the blood vessel wall cannot hold and the blood vessel will fail at the aneurysm location, often with fatal result.

Various implantable medical devices and minimally invasive methods for implantation of these devices have been developed to deliver these medical devices with the lumen of a body vessel. These devices are advantageously inserted intravascularly, for example, from an implantation catheter. For example, to prevent rupture of an aneurysm, a stent graft of a tubular construction may be introduced into the blood vessel and deployed and secured in a location within the blood vessel such that the stent graft spans the aneurysmal sac. The outer surface of the stent graft, at its opposed ends, abuts and seals against the interior wall of the blood vessel at a location where the blood vessel wall has not suffered a loss of strength or resiliency. The stent graft channels the blood flow through the hollow interior of the stent graft, thereby reducing, if not eliminating, any stress on the blood vessel wall at the aneurysmal sac location.

Bifurcated medical devices may be implanted for the repair of an aneurysm at or in the vicinity of the aortic bifurcation. Typically, a bifurcated device comprises a main body and two tubular legs joining the main body in a bifurcation. In many instances, both the main body and each of the legs are stented. Due to this design, intravascular implantation may be complicated because the bifurcated device may have a relatively large delivery profile. A large delivery profile makes treating patients with tortuous anatomy or those having smaller arteries very difficult and, in some cases, impossible. A decrease in the delivery profile of a bifurcated device provides possibilities of treatment for these patients they made not have had. Additionally, a smaller more flexible device may reduce the incidence of iliac artery ruptures or damage.

SUMMARY

The present disclosure relates to an implantable medical device for regulating fluid flow through a body vessel. More specifically, certain aspects relate to an intraluminal medical device comprising a main graft and two extension grafts that allow for a reduced delivery profile of the medical device.

In one aspect, an intraluminal medical device is provided. The medical device comprises a main graft, a first extension graft, and a second extension graft. The main graft comprises a proximal end, a distal end, and a body extending between the proximal end and distal end. The distal end of the main graft comprises a first branch and a second branch, the branches extending distally from the body. The first and second extension grafts comprise at least one stent and have a body reinforcing portion and a branch reinforcing portion. The body reinforcing portions have a larger expanded dimension than the expanded dimension of the respective branch reinforcing portion. The body reinforcing portions, together, have an expanded dimension that is generally equal to the expanded dimension of the outer graft body.

In another aspect, a multi-stage intraluminal grafting system is provided. The grafting system comprises a first stage and a second stage. The first stage comprises a main graft having a body, a first branch extending distally from the body, and a second branch extending distally from the body. The second stage comprises a first extension graft and a second extension graft. The first extension graft reinforces the first branch and at least a portion of the main graft body and defines a first branch lumen. The second extension graft reinforces the second branch and at least a portion of the main graft body and defines a second branch lumen. The first extension graft interacts with the second extension graft within the main graft body to divide fluid flow within the main graft body.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The medical device may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION

The present disclosure provides for a medical device and method for bridging a defect in a main vessel near one or more branch vessels, for example at or in the vicinity of a bifurcation in the arterial system of a patient. The present disclosure is described below in reference to its application in connection with endovascular treatment of abdominal aortic aneurysms and dissections. However, it is likewise applicable to any suitable endovascular treatment or procedure including, without limitation, endovascular treatment of thoracic aortic aneurysms and dissections.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Definitions

"Implantable" refers to an ability of a prosthetic implant to be positioned, for any duration of time, at a location within a body, such as within a body vessel. Furthermore, the terms "implantation" and "implanted" refer to the positioning, for any duration of time, of a prosthetic implant at a location within a body, such as within a body vessel.

"Body vessel" means any tube-shaped body passage lumen that conducts fluid, including but not limited to blood vessels such as those of the human vasculature system, esophageal, intestinal, billiary, urethral and ureteral passages.

"Branch vessel" refers to a vessel that branches off from a main vessel. The "branch vessels" of the thoracic and abdominal aorta include the iliac, celiac, inferior phrenic, superior mesenteric, lumbar, inferior mesenteric, middle sacral, middle suprarenal, renal, internal spermatic, ovarian (in the female), innominate, left carotid, and left subclavian arteries. As another example, the hypogastric artery is a branch vessel to the common iliac, which is a main vessel in this context. Thus, it should be seen that "branch vessel" and "main vessel" are relative terms.

"Stent" means any device or structure that adds rigidity, expansion force, or support to a prosthesis.

"Stent graft" refers to a prosthesis comprising a stent and a graft material associated therewith that forms a lumen through at least a portion of its length.

The terms "about" or "substantially" used with reference to a quantity includes variations in the recited quantity that are equivalent to the quantity recited, such as an amount that is insubstantially different from a recited quantity for an intended purpose or function.

"Proximal" means that position or portion of a component which is closest to the patient's heart.

"Distal" means that position of portion of a component which is furthest from the patient's heart.

"Biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part 1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

"Inextensible" means substantially incapable of being extended or stretched under typical physiological loads. In one example, an inextensible material may have a stretch ratio not greater than 1.1. Stretch ratio is defined as the ratio of a material's deformed length to undeformed (e.g., no strain) length.

"Extensible" means capable of being extended or stretched under typical physiological loads.

Intraluminal Medical Devices

Medical devices according to the present disclosure may be any device that is introduced temporarily or permanently into the body for the prophylaxis or therapy of a medical condition, for example abdominal aortic aneurysms. Typical subjects (also referred to herein as "patients") are vertebrate subjects (i.e., members of the subphylum cordata), including, mammals such as cattle, sheep, pigs, goats, horses, dogs, cats and humans.

Figure 1:
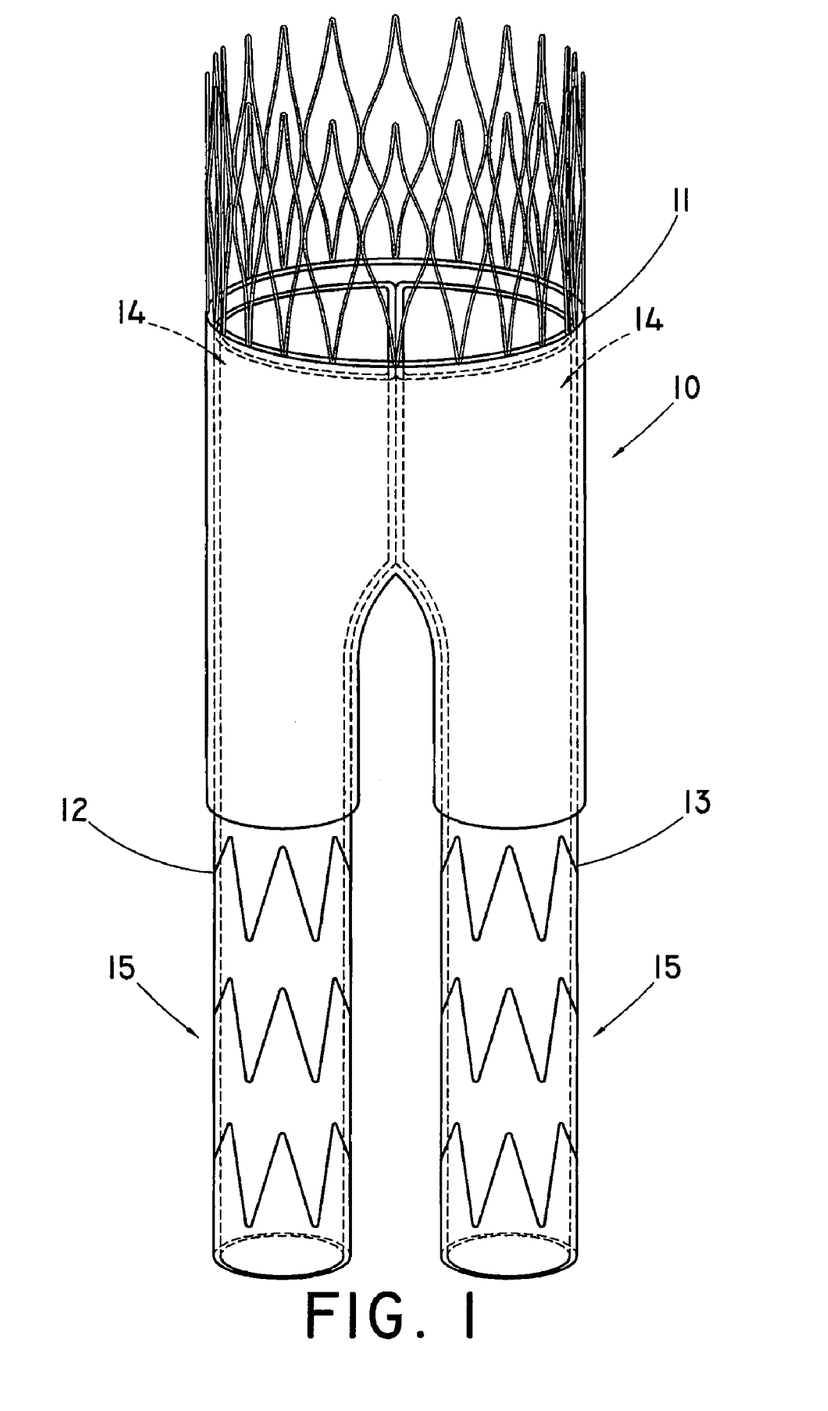
FIG. 1 depicts a bifurcated low profile endovascular device.

FIG. 1 depicts an exemplary medical device. Medical device 10 may be positioned within a body vessel, such as a patient's aorta, to reinforce a weak spot or lesion in the body vessel at or near an aneurysm. In one example, the medical device 10 is positioned within the body vessel at or in the vicinity of a bifurcation for example where the aorta meets the right and left common iliac arteries. The medical device 10 may provide strength to the injured or diseased body vessel at the aneurysm and may allow fluid to flow through the medical device 10 without further stress and/or trauma to the aneurysm, thus preventing enlargement and/or rupture of the body vessel at the lesion site. In a further example, the medical device 10 may be used for the treatment of a dissection.

As shown in FIG. 1, the medical device comprises a main graft 11, a first extension graft 12, and a second extension graft 13. The first and second extensions 12, 13 each include a proximal body portion 14 and a distal leg portion 15. The proximal body portion 14 of the first extension graft 12, second extension graft 13, and a part of the distal leg portions 15 may be located within and overlap with the main graft 11.

The main graft 11, first extension graft 12, and second extension graft 13 may have any suitable length corresponding to a length of the lesion site at which the medical device is to be positioned. The medical device 10 may be anchored to an interior wall surface of a body vessel proximally and/or distally to a lesion site. For example the main graft 11 may be anchored to a main vessel wall proximal to an aneurysm and the first and second extension grafts 12, 13 may be anchored distal to the aneurysm, for example to branch vessels.

Main Graft

Figure 2:
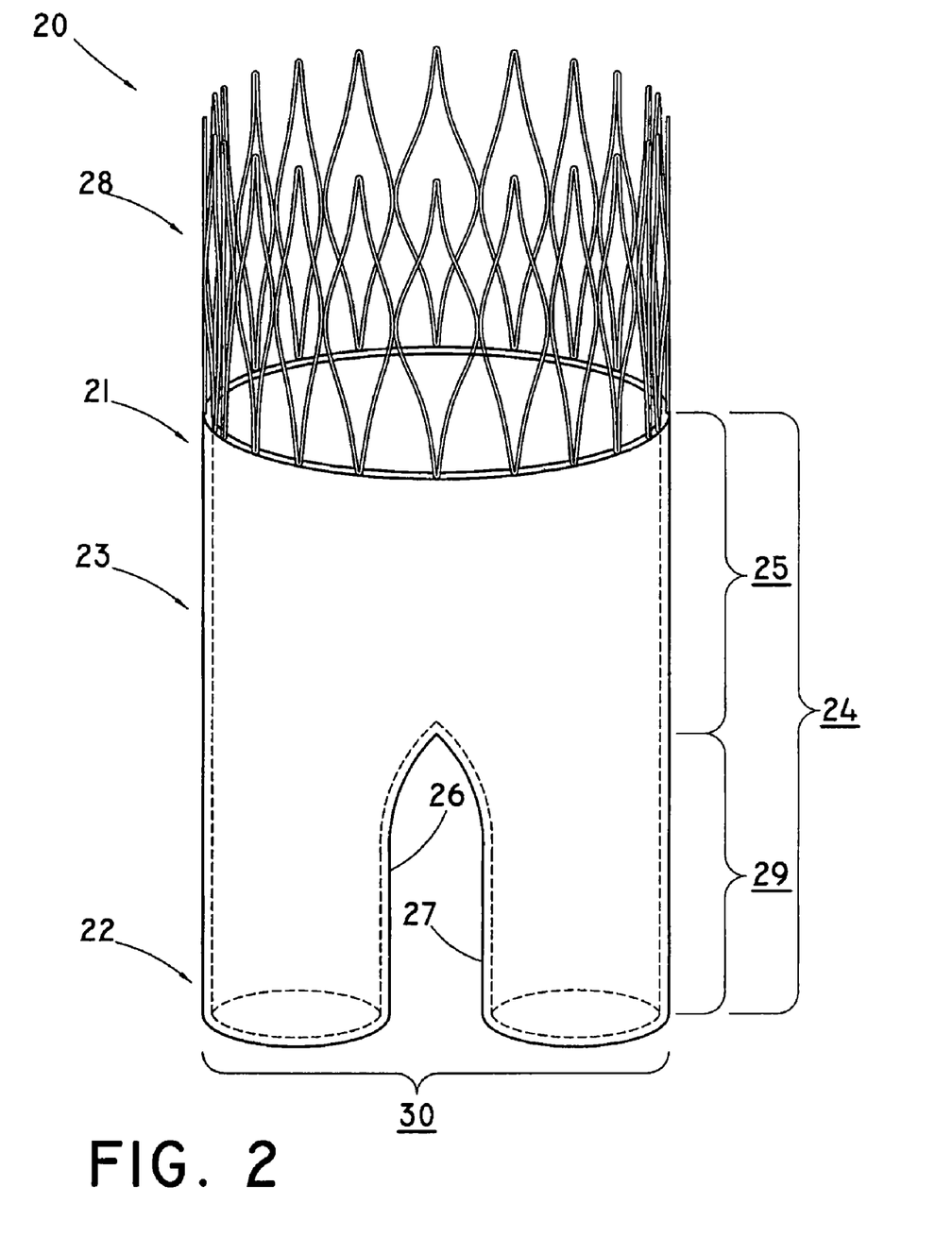
FIG. 2 shows the main body of the medical device.

FIG. 2 illustrates the main graft. As shown, the medical device comprises a main graft 20. The main graft includes a proximal end 21, a distal end 22, and a body 23. The main graft may have any suitable length 24, but in one example the main graft may have a length 24 of about 2 inches, and the body may have a length 25 of about 1.5 inches.

Still referring to FIG. 2, the main graft distal end 22 has two branches 26, 27 extending distally from the body 23. The branches 26, 27 may be identical or differ. For example, the branches may have the same or different lengths, the same or different widths, may be symmetrical or asymmetrical, or may comprise the same or different materials. In the example of FIG. 2, the branches 26, 27 are of equal length and width.

As shown, the main graft proximal end 21 may include an anchor, such as a stent 28. Suitable anchors also include any means for attaching a medical device to a body vessel wall, for example suturing, stapling, searing, bonding, gluing, bioadhesives, and the like. The anchor may be attached or adhered to the main graft by any means, including but not limited to welding, stitching, bonding, and adhesives.

Figure 5A:
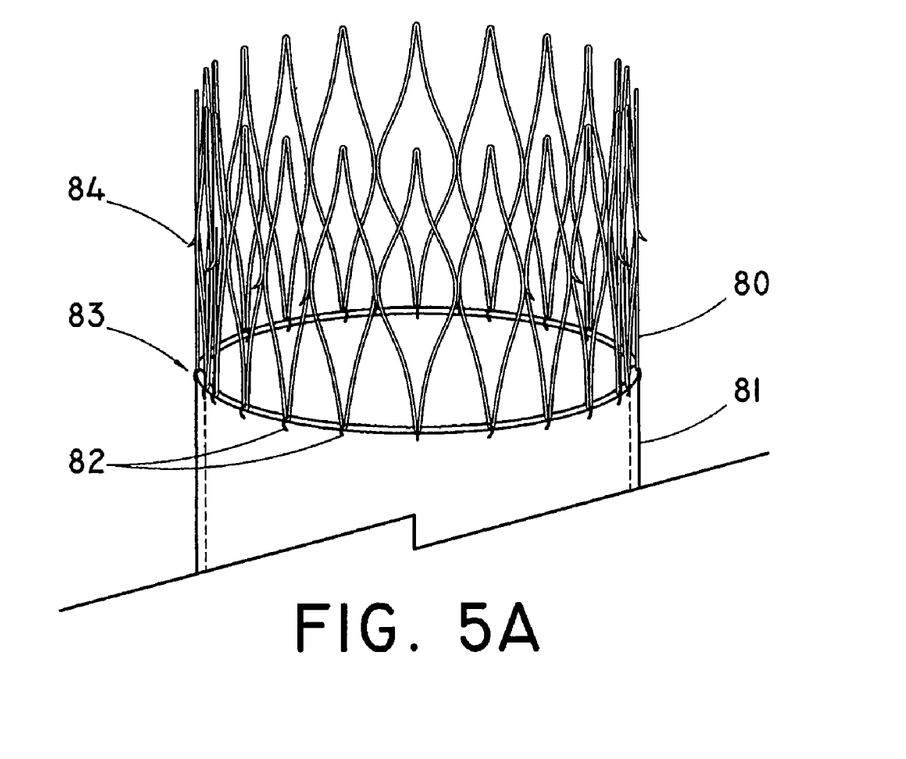
FIGS. 5A and 5B depict an anchor sutured to the main graft proximal end.
Figure 5B:
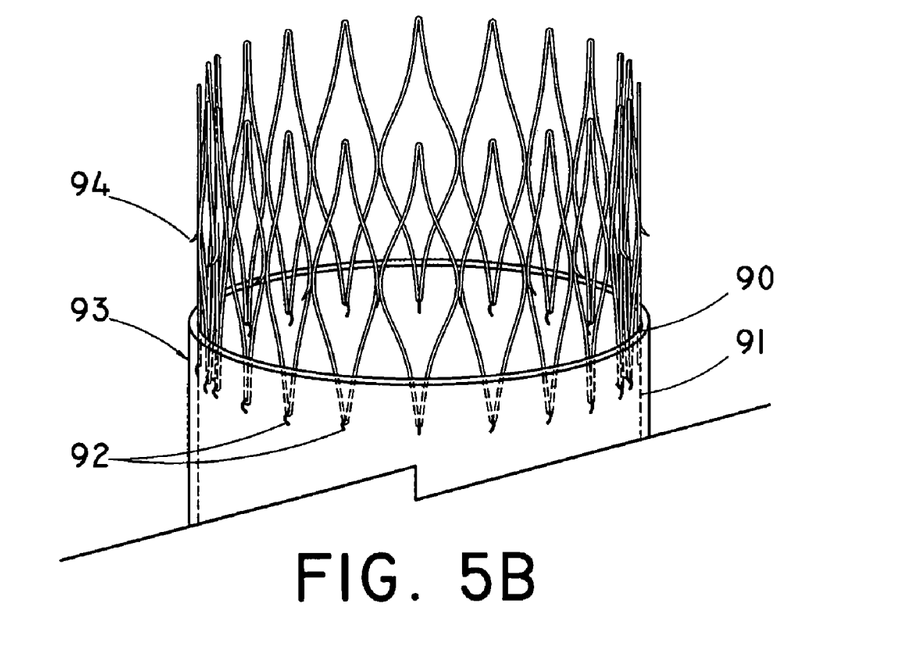

FIGS. 5A and 5B depict an exemplary anchor. The anchor comprises a stent 80 attached to the graft 81 by sutures 82 to the main graft proximal end 83. In one aspect, depicted in FIG. 5A, the stent 80 may be spaced from the main graft proximal end 83 such that stent 80 does not overlap the main graft proximal end 83. Sutures 82 may space the stent 80 from the main graft proximal end 83, permitting a reduced delivery profile for the main graft. Alternatively, FIG. 5B illustrates the stent 80 sutured to the main graft proximal end 83 and having an overlap with the main graft proximal end 83.

Extension Grafts

Figure 3:
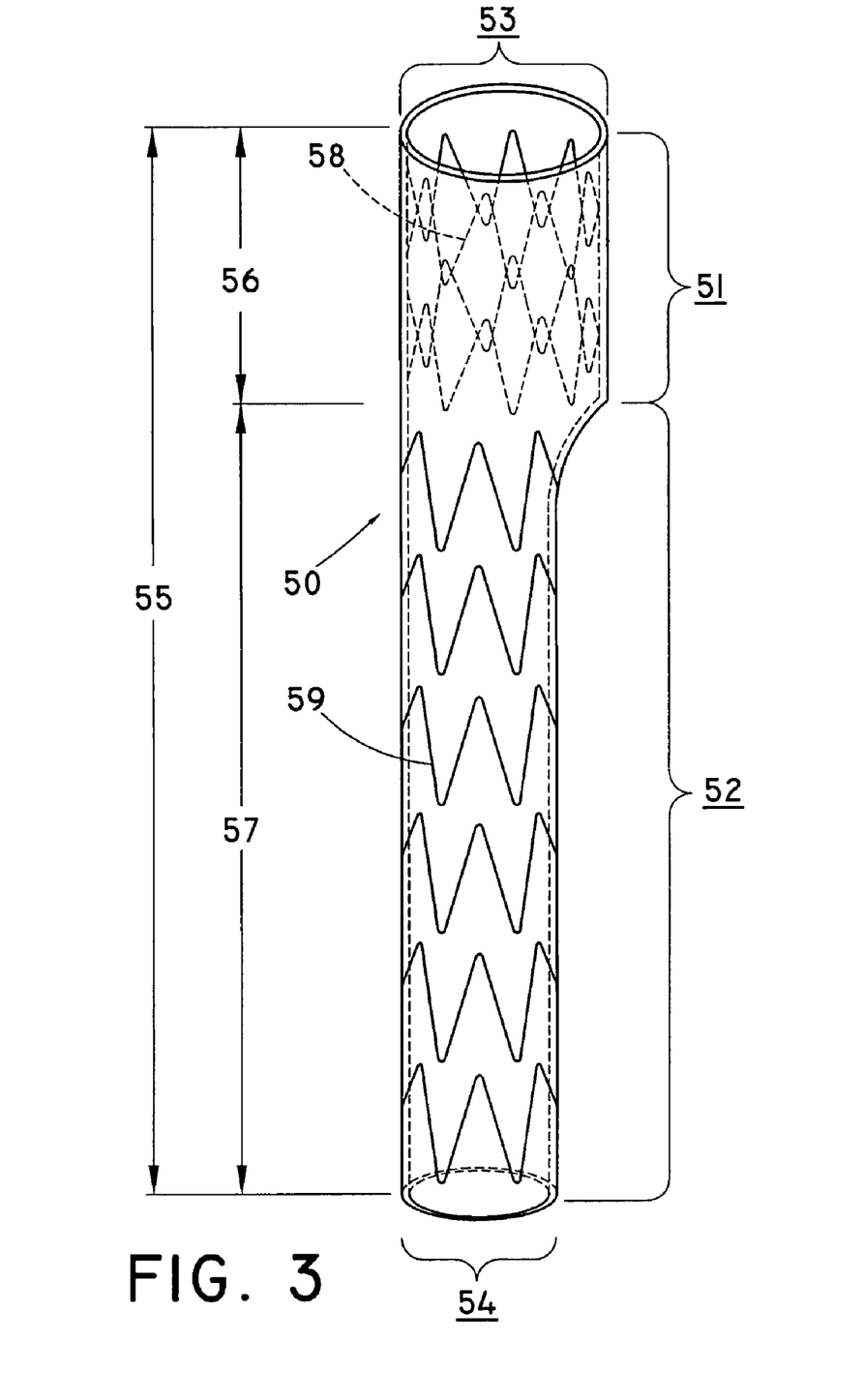
FIG. 3 shows a first extension graft of the medical device.
Figure 4:
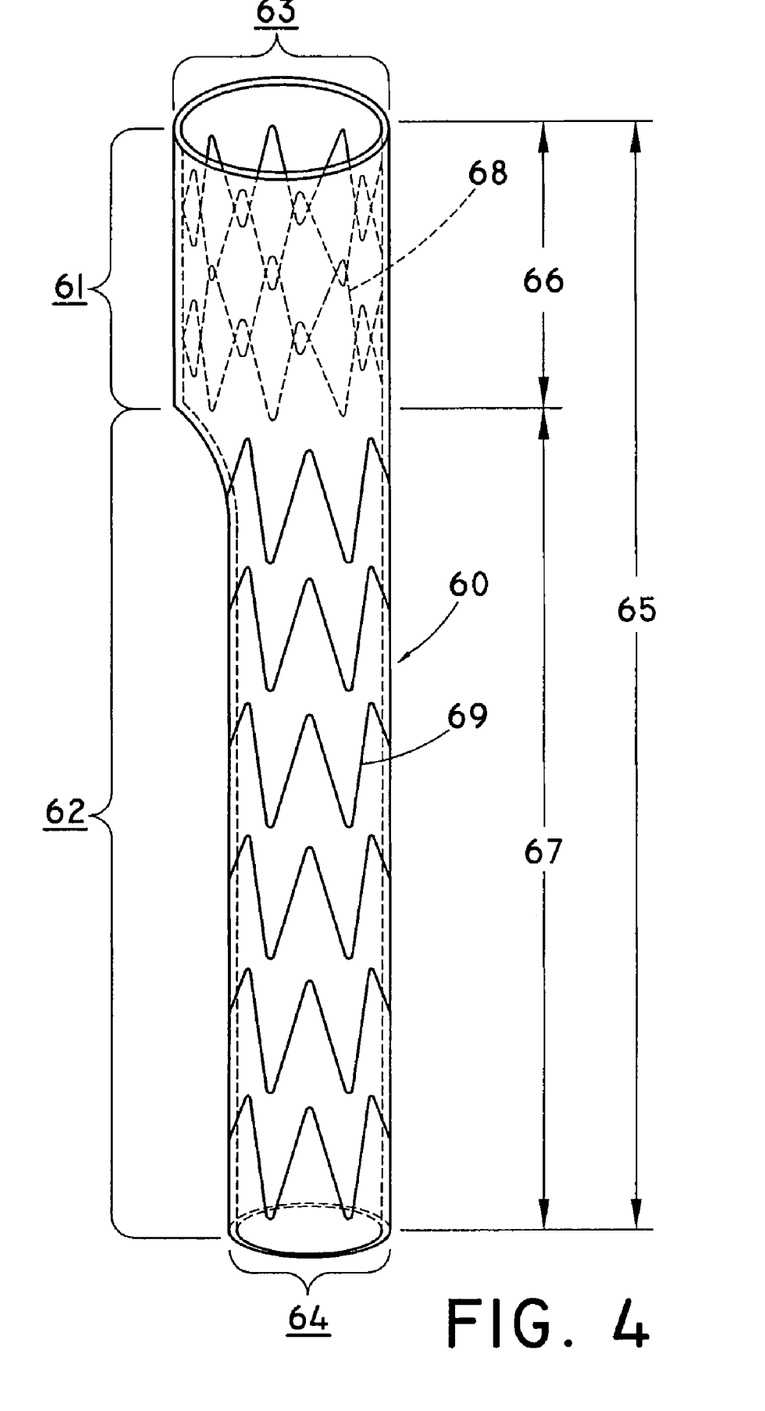
FIG. 4 shows a second extension graft of the medical device.

As described above, the medical device 10 may comprise a first extension graft 12 and a second extension graft 13. FIGS. 3 and 4 depict a first extension graft 50 and second extension graft 60, respectively, independent of the main graft 20. The extension grafts 50, 60 comprise a body reinforcing portion 51, 61 and a branch reinforcing portion 52, 62. The extension grafts may be identical or differ. For example, the extension grafts may have the same or different lengths, the same or differing widths, may be symmetrical or asymmetrical, or may comprise the same or differing materials.

In one example, the extension grafts 50, 60 have a compressed and an expanded configuration. The extension grafts 50, 60 may radially expand from a compressed, or unexpanded, delivery configuration to one or more expanded deployment configurations. In one example, the extension grafts 50, 60 comprise stents 58, 68 located about the body reinforcing portions 51, 61 and stents 59, 69 located about the branch reinforcing portions 52, 62. For example, as depicted in FIGS. 3 and 4, stents 58, 68 may be located on the interior, or luminal, surface of the body reinforcing portions 51, 61, respectively. Stents 59, 69 may be located on the exterior, or abluminal, surface of the branch reinforcing portions 52, 62.

In one example, stents 59, 69 may be self-expanding and stents 58, 68 may be balloon expandable. Upon compression, self-expanding stents may expand toward their pre-compression geometry. In another example, stents 59, 69 may be balloon expandable and/or stents 58, 68 may be self-expanding. In examples where stents 59, 69 and/or 58, 68 comprise self-expanding stents, a balloon may be used to urge the stents toward one another to provide optimal alignment of the extension grafts 50, 60.

The body reinforcing portions 51, 61 may have an expanded diameter 53, 63 that is at least as great as the expanded width or diameter 54, 64 of the branch reinforcing portions 52, 62. For example, the body reinforcing portions 51, 61 may have a combined width (e.g., width 53 plus width 63) that is at least as great as the diameter 30 of the main graft body 23. Alternatively, the combined width or diameter of the body reinforcing portions may be generally equal to the main graft body width 30.

The extension grafts 50, 60 may have any suitable length 55, 65. For example, the extension grafts 50, 60 may have a length 55, 65 that is at least as great as the main graft length 24. The extension graft length 55, 65 includes a body reinforcing portion length 56, 66 and a branch reinforcing portion length 57, 67. The body reinforcing portion lengths 56, 66 may be equal to or less than the main graft body length 25. Alternatively, the body reinforcing portions' lengths 56, 66 may be greater than the main graft body length 25.

The branch reinforcing portion lengths 67, 77 may be the same or different. For example, in FIG. 3, the first extension graft 50 has branch reinforcing portion length 57 that is greater than the branch reinforcing portion length 67 of the second extension graft 60 shown in FIG. 4. The branch reinforcing portion lengths 57, 67 may be equal to or greater than the length 29 of the branches 26, 27 extending distally from the main graft 20.

Stents

In general, stents for use in connection with the present disclosure, such as anchor 28, stents 58, 59, 68, 69, or otherwise, typically comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube).

The stents may be self-expanding or balloon-expandable, and may be deployed according to conventional methodology, such as by an inflatable balloon catheter, by a self-deployment mechanism (after release from a catheter), or by other appropriate means. The stents may be bifurcated, configured for any blood vessel including coronary arteries and peripheral arteries (e.g., renal, superficial femoral, carotid, and the like), a urethral stent, a biliary stent, a tracheal stent, a gastrointestinal stent, or an esophageal stent, for example. The stents may be any suitable vascular stent such as the commercially available Gianturco-Roubin FLEX-STENT® or SUPRA-G stents from Cook Incorporated (Bloomington, Ind.). For example, the stent 80 depicted in FIGS. 3A and 3B comprises a modified chuter stent having eyelets.

The stents may be made of one or more suitable biocompatible materials such as stainless steel, nitinol, MP35N, gold, tantalum, platinum or platinum irdium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the stents comprise stainless steel or nitinol.

Stents may optionally include supplemental attachment means such as anchoring devices. The art provides a wide variety of structural features that are acceptable for use in medical devices as anchoring devices, and any suitable structural feature can be used. For example, individual barbs may be used to implant the medical device into a vessel. The barbs may be secured to the medical device by any means known to one skilled in the art, including but not limited to welding, stitching, bonding, and adhesives. Furthermore, barbs can also comprise separate members attached to the medical device by suitable attachment means.

In one example, anchor 28 may comprise features, such as barbs, that maintain the medical device in position following implantation in a body vessel. For example, FIGS. 5A and 5B depict stent 80 comprising barbs 84 to facilitate maintenance of the device in the body vessel.

Bioadhesives

Alternatively or in addition to anchoring members, bioadhesives may be used for attachment. Bioadhesive may be included in any suitable part of the prosthesis. Preferably, the bioadhesive is attached to the abluminal surface of the textile graft. Selection of the type of bioadhesive, the portions of the prosthesis comprising the bioadhesive, and the manner of attaching the bioadhesive to the prosthesis can be chosen to perform a desired function upon implantation. For example, the bioadhesive can be selected to promote increased affinity of the desired portion of prosthesis to the section of the body vessel against which it is urged.

Bioadhesives for use in conjunction with the present disclosure include any suitable bioadhesives known to those of ordinary skill in the art. For example, appropriate bioadhesives include, but are not limited to, the following: (1) cyanoacrylates such as ethyl cyanoacrylate, butyl cyanoacrylate, octyl cyanoacrylate, and hexyl cyanoacrylate; (2) fibrinogen, with or without thrombin, fibrin, fibropectin, elastin, and laminin; (3) mussel adhesive protein, chitosan, prolamine gel and transforming growth factor beta(TGF-B); (4) polysaccharides such as acacia, carboxymethyl-cellulose, dextran, hyaluronic acid, hydroxypropyl-cellulose, hydroxypropyl-methylcellulose, karaya gum, pectin, starch, alginates, and tragacanth; (5) polyacrylic acid, polycarbophil, modified hypromellose, gelatin, polyvinyl-pylindone, polyvinylalcohol, polyethylene glycol, polyethylene oxide, aldehyde relative multifunctional chemicals, maleic anhydride co-polymers, and polypeptides; and (6) any bioabsorbable and biostable polymers derivitized with sticky molecules such as arginine, glycine, and aspartic acid, and copolymers.

Furthermore, commercially available bioadhesives that may be used in the present disclosure include, but are not limited to: FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanocrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by Medi-West Pharma; and VETBOND® which consists of n-butyl cyanoacrylate produced by 3M.

Graft Material

The main graft 11 and first and second extension grafts 12, 13 may include any suitable biocompatible material which is suitable for facilitating repair to the injured or diseased body vessel. The graft material may be synthetic, naturally-derived material, and/or manufactured.

For example, synthetic biocompatible polymers include, but are not limited, cellulose acetate, cellulose nitrate, silicone, polyethylene teraphthalate, polyurethane, polyamide, polyaramide, polyacrylonitrile, nylon, polyester, polyorthoester, polyanhydride, polyether sulfone, polycarbonate, polypropylene, high molecular weight polyethylene, polytetrafluoroethylene, or mixtures or copolymers thereof.

In one example, the graft material comprises one or more polymers that do not require treatment or modification to be biocompatible. For example, the graft material may comprise biocompatible polymers, such as polyethylene terephthalate and PTFE. These materials are inexpensive, easy to handle, have good physical characteristics and are suitable for clinical application. A commercial example of polyethylene terephthalate especially is Dacron.

In one example, the main graft 20 comprises an inextensible material, such as Dacron®. For example, upon deployment, the main graft 11 may reach its tailored full diameter 30. The inextensible material may not permit the main graft 11 to expand further in size under internal loading, such as from blood pressure or stent loading.

In another example, the first extension graft 50 and second extension graft 60 may comprise a hybrid material, for example a hybrid weave which is extensible at the body reinforcing portion 51, 61, such as spandex, and transitions to an inextensible fabric at the branch reinforcing portion 52, 62, such as Dacron®. In this example, if during a delivery procedure described below, an adequate proximal seal is not obtained, a balloon may be inserted into each extension graft 50, 60, either separately or in parallel (simultaneously), and when inflated the body reinforcing portions 51, 61 may expand beyond their nominal diameter 53, 63 and enhance the proximal seal, for example sealing the main graft body 23 to a vessel wall.

Delivery of Medical Device

The medical device 10 maybe be configured for delivery to a body vessel. For example, a medical device may be compressed to a delivery configuration within a retaining sheath that is part of a delivery system, such as a catheter-based system. Upon delivery, the medical device can be expanded, for example, by use of self-expanding stents and/or inflating a balloon from inside the stents. The delivery configuration can be maintained prior to deployment of the medical device by any suitable means, including a sheath, a suture, a tube or other restraining material around all or part of the compressed prosthesis, or other methods.

Medical devices can be deployed in a body vessel by means appropriate to their design. Medical devices of the present disclosure can be adapted for deployment using conventional methods known in the art and employing percutaneous transluminal catheter devices. The medical devices are designed for deployment by any of a variety of in situ expansion means.

For example, a medical device may be mounted onto a catheter that holds the medical device as it is delivered through the body lumen and then releases the medical device, permitting the medical device to expand and contact the body lumen. This deployment is effected after the medical device has been introduced percutaneously, transported transluminally and positioned at a desired location by means of the catheter. For example, the medical device may be positioned at the distal end of a catheter with a removable sheath or sleeve placed over the medical device to hold the medical device in a compressed delivery configuration with a relatively small diameter. The medical device may then be implanted at the point of treatment by advancing the catheter over a guide wire to the location of the lesion, aligning the medical device with any branch vessels, and then withdrawing the sheath from over the medical device. The medical device may expand and seal against the wall of the blood vessel at the site of treatment. The catheter, sleeve, and guide wire may then be removed from the patient.

In one example, the main graft 20 may be delivered endovascularly to a lesion site in a compressed, or unexpanded, delivery configuration. For example, for treatment of an abdominal aortic aneurysm, a compressed main graft may be delivered via a 9 Fr to about 14 Fr sheath to a location immediately distal the renal arteries. Following placement of the compressed main graft at the desired location of treatment, the sheath may be withdrawn, deploying the main graft 20. The main graft 20 may be held in place at the treatment location by anchor 28 at the delivery location. The main graft may expand due to blood flow through the main graft 20, similar to a wind sock effect.

Following deployment of the main graft 20 at the desired treatment location, the first extension graft 50 and second extension graft 60 may be delivered endovascularly to the treatment location. For example, the first extension graft 50 may be compressed to a delivery configuration in a sheath and delivered to a location near the main graft proximal end 21. Upon locating the first extension graft 50, the sheath may be withdrawn allowing the first extension graft 50 to expand. In one example, the first branch 26 may be cannulated prior to delivery of the first extension graft 50.

The second extension graft 60 may be compressed to a delivery configuration in a sheath and delivered to a location near the main graft proximal end 21. Upon locating the second extension graft 60, the sheath may be withdrawn allowing the second extension graft 60 to expand. In one example, the second branch 27 may be cannulated via an up-and-over guide catheter prior to delivery of the second extension graft 60.

After placement, the first extension graft 50 and second extension graft 60 may expand in the main graft. For example, the branch reinforcing portion 52 may expand and seal the first extension graft 50 in the main graft first branch 26 and the second branch reinforcing portion 62 may expand and seal the extension graft 60 in the main graft second branch 27. The first extension graft body reinforcing portion 51 and second extension graft body reinforcing portion 61 may expand within the main graft body 23.

Figure 6A:
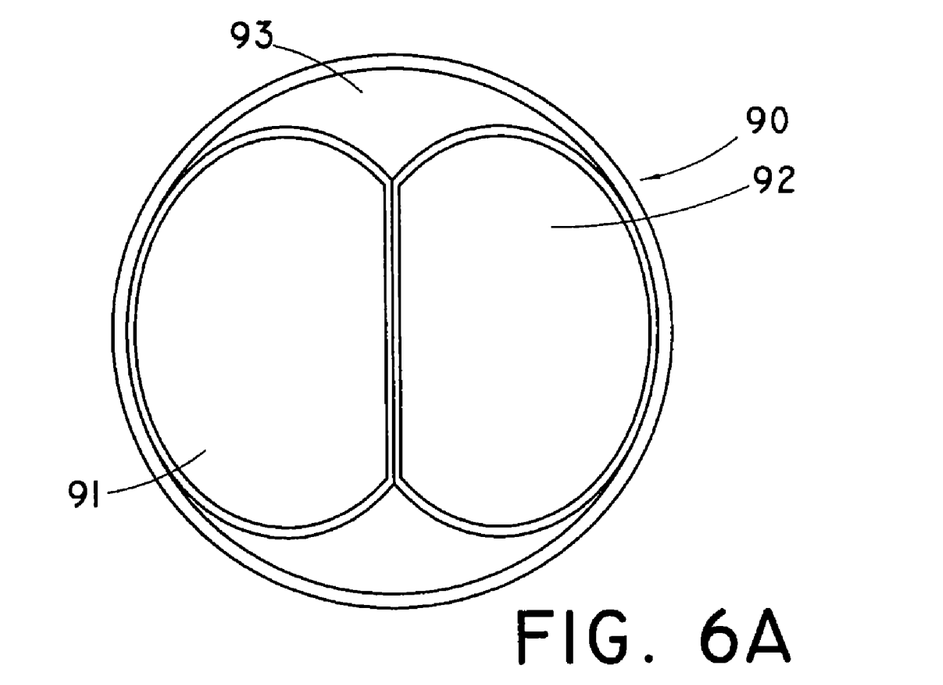
FIGS. 6A and 6B depict the first extension graft and second extension graft expanded within the main graft body.
Figure 6B:
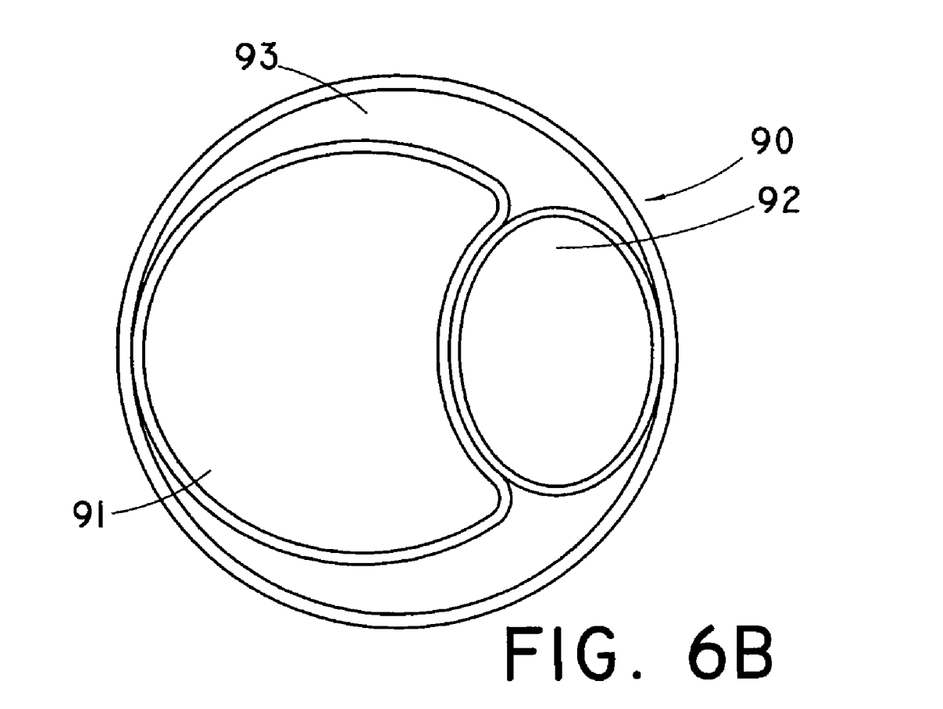

The body reinforcing portions 51, 61 may interact with one another to provide sealing forces about the main graft 20. For example, in FIGS. 6A and 6B, the first extension graft body reinforcing portion 91 interferes with the second extension graft body reinforcing portion 92 within the main graft 90. FIG. 6A depicts the first extension graft body reinforcing portion 91 and the second extension graft body reinforcing portion 92 having a D-shaped radial contour within the main graft 90. Alternatively, the first extension graft body reinforcing portion 91 and the second extension graft body reinforcing portion 92 may expand asymmetrically in the main graft 90, as depicted in FIG. 6B. In examples where graft body reinforcing portions 91, 92 expand asymmetrically, a balloon may be used to position the body reinforcing portions to provide optimal alignment of the body reinforcing portions 91, 92.

Any voids 93 within with main graft may fill with fluid and, in one example, the fluid may clot and prevent any possible fluid leakage.

While various aspects and examples have been described, it will be apparent to those of ordinary skill in the art that many more examples and implementations are possible within the scope of the disclosure. Accordingly, the disclosure is not to be restricted except in light of the attached claims and their equivalents.

We claim:

1. An intraluminal medical device comprising:
    a bifurcated main graft having a compressed configuration and an expanded configuration and comprising a proximal end, a distal end, and a body portion;
    the main graft body portion having an axial length from the proximal end to the bifurcation of the main graft;
    the distal end comprising a first branch and a second branch;
    a first extension graft and a second extension graft, each of the extension grafts having a compressed configuration and an expanded configuration and comprising at least one stent and having a body reinforcing portion having an axial length and a branch reinforcing portion;
    where, in the expanded configuration, each of the body reinforcing portions have a larger expanded dimension than the expanded dimension of the respective branch reinforcing portion;
    where, in the expanded configuration, the body reinforcing portions, together, have an expanded dimension that is generally equal to the expanded dimension of the main graft body;
    where, in the expanded configuration, the body reinforcing portions contact one another and sealingly engage one another within the main graft body to prevent fluid leakage; and
    where, in the expanded configuration, the axial length of the body reinforcing portion is substantially equal to the axial length of the main graft body portion.

2. The medical device of claim 1, where the main graft is unstented between the proximal and distal ends and where body reinforcing portions comprise only internal stents.

3. The medical device of claim 2, where the main graft comprises an anchor.

4. The medical device of claim 1, where the main graft comprises at least one stent.

5. The medical device of claim 1, where the first and second extension graft body reinforcing portions each comprise at least one balloon-expandable stent.

6. The medical device of claim 5, where the first and second extension graft branch reinforcing portions each comprise at least one self-expanding stent.

7. The medical device of claim 1, where the first and second extension graft branch reinforcing portions each comprise at least one balloon-expandable stent.

8. The medical device of claim 1, where the length of the main graft first branch is substantially the same as the length of the main graft second branch.

9. The medical device of claim 1, where, in the expanded configuration, the first and second extension graft body reinforcing portions comprise an expanded radial contour selected from the group consisting of a generally elliptical expanded radial contour, a D-shaped expanded radial contour, and a generally cylindrical expanded radial contour.

10. The medical device of claim 1, where the main graft comprises a material having a stretch ratio not greater than 1.1.

11. The intraluminal medical device of claim 1 where one body reinforcing portion has a greater axial length than the other body reinforcing portion.

12. The intraluminal medical device of claim 1 where in the expanded configuration one body reinforcing portion has a larger dimension the other body reinforcing portion.

13. An intraluminal medical device comprising:
    a bifurcated main graft having a compressed configuration and an expanded configuration and comprising a proximal end, a distal end, and an unstented body extending between the proximal end and the bifurcation of the main graft, the main graft further comprising a graft material having a stretch ratio not greater than 1.1;
    the proximal end comprising an anchor;
    the distal end comprising a first branch and a second branch, the branches extending distally from the body;
    a first extension graft and a second extension graft, each of the extension grafts having a proximal end, a distal end, a compressed configuration and expanded configuration and comprising a body reinforcing portion and a branch reinforcing portion;

the first extension graft and second extension graft body reinforcing portions each comprising at least one balloon expandable stent;

the first extension graft and second extension branch reinforcing portions each comprising at least one self-expanding stent;

where in the expanded configuration the first and second extension graft body reinforcing portions have a larger dimension than the-their respective branch reinforcing portion;

where in the expanded configuration the first extension graft body reinforcing portion contacts and sealingly engages the second extension graft body reinforcing portion within the main graft body to prevent fluid leakage; and where the proximal end of at least one of the first and second extension grafts extends substantially to the proximal end of the main graft.

14. The medical device of claim 13, where the first and second extension grafts each comprise a graft material having a stretch ratio not greater than 1.1.

15. The medical device of claim 13, where the first and second extension grafts each comprise a material having a stretch ratio greater than 1.1.

16. The medical device of claim 13, where the first and second extension graft body reinforcing portions comprise a material having a stretch ratio greater than 1.1 and the first and second extension graft branch reinforcing portions comprise a graft material having a stretch ratio not greater than 1.1.

17. The medical device of claim 13, further comprising a third extension graft having a compressed and expanded configuration, where in the expanded configuration the third extension graft sealingly engages at least one of the first and second extension grafts in the expanded configuration.

18. The medical device of claim 17, where at least a portion of the third extension graft comprises a graft material having a stretch ratio not greater than 1.1 and at least a portion of the third extension graft comprises a graft material having a stretch ratio greater than 1.1.

19. A multi-component intraluminal grafting system comprising:

a first component comprising a main graft having a body, a first branch extending distally from the body, and a second branch extending distally from the body, the main graft having a compressed and an expanded configuration the body having an axial length between a proximal end of the main graft and the first and second branches;

a second component comprising a first extension graft and a third component comprising a second extension graft, each having a compressed and expanded configuration;

where in the expanded configuration the first extension graft reinforces the first branch and substantially the entire axial length of the main graft body and comprises a first branch lumen;

where in the expanded configuration the second extension graft reinforces the second branch and substantially the entire axial length of the main graft body and comprises a second branch lumen; and where in the expanded configuration the first extension graft contacts and interacts with the second extension graft within the main graft to provide sealing forces about the main graft body to prevent fluid leakage and to divide fluid flow within the main graft body.

20. The grafting system of claim 19, where the first extension graft and second extension graft comprise at least one balloon-expandable stent and at least one self-expanding stent.

21. The grafting system of claim 19 further comprising a fourth component comprising a third extension graft, where the third extension graft extends at least one of the first and second extension grafts.

* * * * *